(12) United States Patent
Thyes et al.

(10) Patent No.: US 6,476,033 B1
(45) Date of Patent: Nov. 5, 2002

(54) MEDICAMENTS CONTAINING DOXAZOSIN MESYLATE OF CRYSTALLINE MODIFICATION D

(75) Inventors: Marco Thyes, Ludwigshafen (DE); Heinz Einig, Neustadt (DE); Peter Klein, Birkenheide (DE); Dieter Hix, Grosskarlbach (DE)

(73) Assignee: Chemische Fabrik Berg GmbH, Bitterfeld (DE)

( * ) Notice: Subject to any disclaimer, the term of this patent is extended or adjusted under 35 U.S.C. 154(b) by 0 days.

(21) Appl. No.: 09/936,792
(22) PCT Filed: Mar. 6, 2000
(86) PCT No.: PCT/EP00/01938
§ 371 (c)(1), (2), (4) Date: Sep. 18, 2001
(87) PCT Pub. No.: WO00/56293
PCT Pub. Date: Sep. 28, 2000

(30) Foreign Application Priority Data

Mar. 19, 1999 (DE) .......................................... 199 12 573

(51) Int. Cl.$^7$ ................................................ A61K 31/00
(52) U.S. Cl. ................................... 514/252.17; 544/291
(58) Field of Search ....................... 544/291; 514/252.17

(56) References Cited

FOREIGN PATENT DOCUMENTS

WO        0848001     * 10/1997

OTHER PUBLICATIONS

Grcman et al. Study of polymorphism of 1–(4–amino–6, 7–dimethoxy–2–quinazolinyl)–4–[2,3–dihydro–1, 4–benzodioxin–2–yl)carbonyl]–piperazine monomethanesulfonate, FARM. VESTN, 48: 292–293, 1997.*

* cited by examiner

*Primary Examiner*—Mukund J. Shah
*Assistant Examiner*—Hong Liu
(74) *Attorney, Agent, or Firm*—Keil & Weinkauf

(57) ABSTRACT

Drugs comprising modification D of doxazosin mesylate are described. They are suitable for treating high blood pressure.

2 Claims, 3 Drawing Sheets

MEDICAMENTS CONTAINING DOXAZOSIN MESYLATE OF CRYSTALLINE MODIFICATION D

Figure 1:
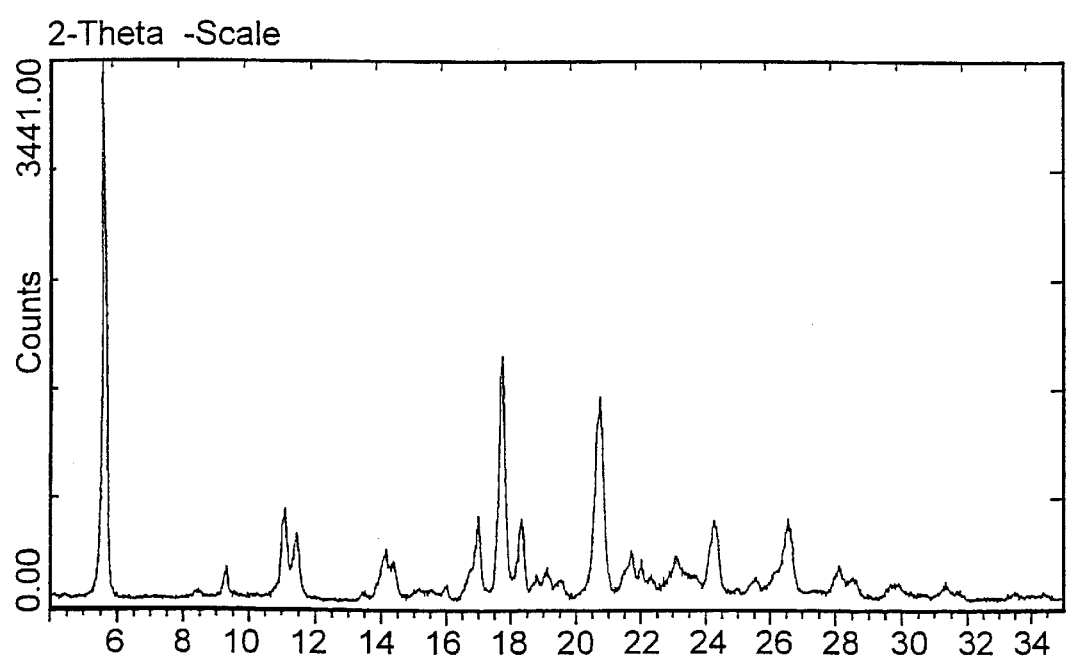

The present invention relates to a drug comprising doxazosin mesylate in crystal modification D.

Doxazosin (=4-amino-2-[4-(1,4-benzodioxan-2-carbonyl)piperazin-1yl-]6,7-dimethoxyquinazoline) is a known substance (Merck Index, 12$^{th}$ edition 1996, No. 3489) which lowers blood pressure. The substance is mainly used in the form of the monomesylate which, in crystalline form, occurs in several modifications. Thus, three crystal modifications which are referred to as modifications A, B and C are described in the Chinese Journal of Medicinal Chemistry 5(4), 266–270 (1995). Modification A is obtained on recrystallization of doxazosin mesylate from ethanol. Modifications B and C result on recrystallization of doxazosin mesylate from chloroform and water respectively. Mention may be made of the fact that the Chinese Journal of Medicinal Chemistry in fact speaks simply of doxazosin. However, according to the published data, the material must be doxazosin mesylate. Modification A is also the subject of EP-A 0 849 266, where it is referred to as form III.

Another modification has been described and characterized in EP-A 0 848 001, but it was not given a special name. EP-A 0 849 264 describes a form I and EP-A 0 849 265 describes a form II of doxazosin mesylate.

The patent application PCT/EP/98/08360 (filed on Dec. 18, 1998), unpublished at the priority date of the present specification, describes a form D of doxazosin mesylate which occurs as intermediate in the preparation of form A of doxazosin mesylate.

It has now been found that modification D of doxazosin mesylate can be used particularly satisfactorily as a drug for high blood pressure.

The invention relates to drugs comprising modification D of doxazosin mesylate and the use of modification D of doxazosin mesylate for producing drugs for high blood pressure.

Modification D of doxazosin mesylate is prepared by dissolving doxazosin with methanesulfonic acid in methanol, removing any turbidity from the resulting solution, stirring the resulting clear solution until no further precipitate is formed, and removing the precipitate and washing it with methanol and drying it.

To react doxazosin with methanesulfonic acid, the two substances are employed in the molar ratio of about 1:1. It is preferred to use a small molar excess of sulfonic acid (up to about 10%).

If the time between the obtaining of a solution by addition of methanesulfonic acid to the doxazosin and the appearance of a precipitate is insufficient for a filtration—for example when the reaction is to be carried out on the industrial scale—the time for the filtration can be extended by adding an aprotic polar organic solvent to the methanol used for the reaction.

Examples of aprotic polar organic solvents suitable in this case are N,N-dimethylformamide and, in particular, N-methyl-2-pyrrolidone. The ratio of doxazosin to methanol (weight/volume) or the ratio of doxazosin to methanol to the aprotic polar organic solvent (weight/volume/volume) is about 1: (5 to 15), preferably about 1:(8 to 12) or about 1:(5 to 15) (1.5 to 4), preferably about 1:(8 to 12):(2 to 3).

If in the process the solution obtained after the addition of methanesulfonic acid has to be filtered to remove any foreign particles present, it is preferred to use the solvent mixture comprising aprotic polar organic solvent and methanol. The reason is that in this case, as already mentioned, the time between the obtaining of the solution and the formation of the first crystals is greater than with the use of methanol alone as solvent. If filtration of the solution obtained after the addition of methanesulfonic acid is desired in the process, a particularly preferred procedure comprises using the solvent mixture of aprotic polar organic solvent and, moreover, adding part of the methanol only after the filtration.

Modification D of doxazosin mesylate is characterized in particular by principal lines in the Debye-Scherrer X-ray diffractogram at the following values of 2 theta stated in degrees: 5.72±0.2°; 11.10±0.2°; 11.46±0.2°; 14.14±0.2°; 17.01±0.2°; 17.78±0.2°; 18.33±0.2°; 20.73±0.2°; 21.70±0.2°; 23.12±0.2°; 24.28±0.2°; 26.58±0.2°.

Modification D of doxazosin mesylate has the advantage that it can be processed to tablets more easily. Thus, this modification shows very good miscibility with other substances and an excellent mixing behavior. The very good flow characteristics of the novel modification further facilitate the production of solid pharmaceutical forms.

EXAMPLES

Preparation of Doxazosin Mesylate of Crystal Modification D

Process a 14.1 g of anhydrous methanesulfonic acid were added to a stirred mixture of 63.2 g of doxazosin, 125 ml of N-methyl-2-pyrrolidone and 500 ml of methanol in a 1 1 three-necked round-bottomed flask. During this time the internal temperature rose to 30° C., and a solution formed. After the addition of the methanesulfonic acid was complete, the reaction mixture was filtered into a second 1 1 three-necked round-bottomed flask. The filter was washed with 85 ml of methanol, and the combined filtrates were stirred for 5 h. After completion of the stirring time, the resulting precipitate was filtered off with suction and washed 3× with 25 ml of methanol each time. 125 g of moist doxazosin mesylate (modification D) were obtained. This corresponds to 70.4 g of dry substance and a yield of 91.8%.

Figure 2:
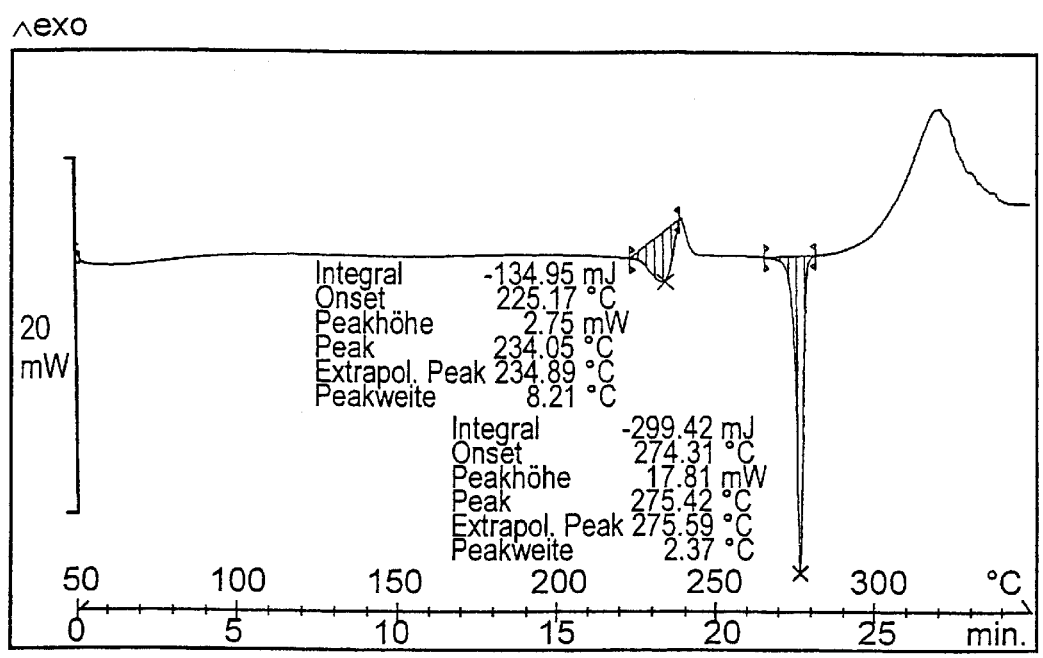
Figure 3:
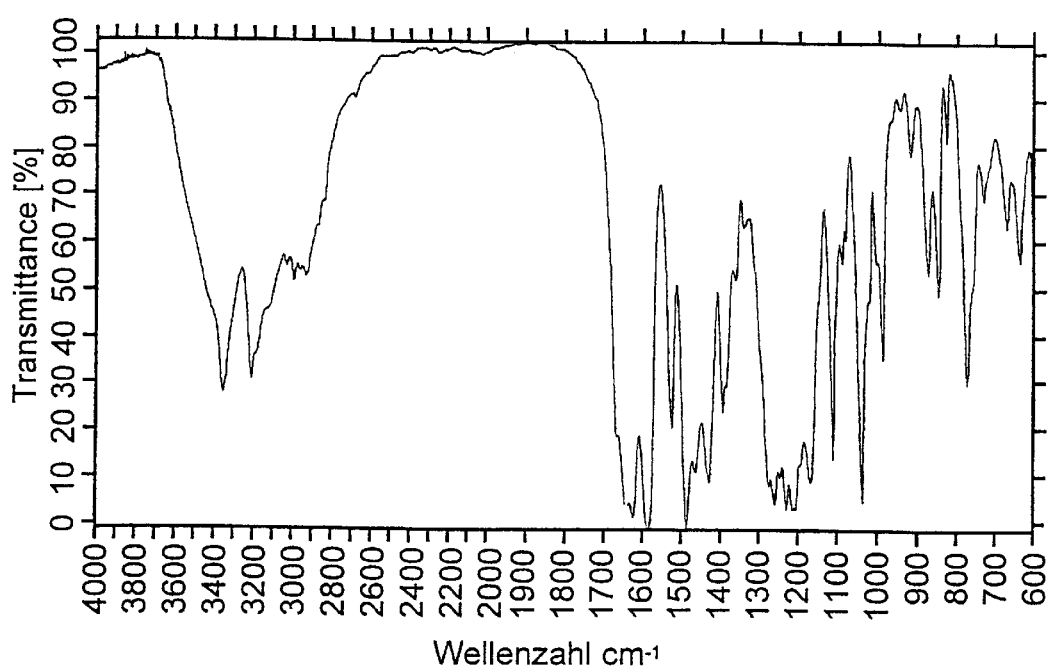

Modification D of doxazosin mesylate was characterized by the Debye-Scherrer X-ray diffractogram, by the differential scanning thermogram and by the IR spectrum (cf. FIGS. 1–3; see above for the 2-theta values of the principal lines in the diffractogram). All the data were obtained for vacuum-dried material.

Process b 6.1 g of anhydrous methanesulfonic acid were added to a stirred mixture of 27.1 g of doxazosin, 54 ml of N-methyl-2-pyrrolidone and 250 ml of methanol in a 500 ml three-necked round-bottomed flask. During this, the internal temperature rose to 30° C., and a solution formed. After the addition of the methanesulfonic acid was complete, the reaction mixture was filtered into a second 500 ml three-necked round-bottomed flask, and the filtrate was stirred for 5 h. After completion of the stirring time, the resulting precipitate was filtered off with suction and washed 2× with 50 ml of methanol each time. 45 g of moist doxazosin mesylate (modification D) were obtained. This corresponds to 28.5 g of dry substance and a yield of 86.7%.

Process c 17.7 g of anhydrous methanesulfonic acid were added to a stirred mixture of 79.0 g of doxazosin and 800 ml of methanol in a 2 1 three-necked round-bottomed flask. During this, the internal temperature rose to 30° C., and a solution formed. After the addition of the methanesulfonic acid was complete, the mixture was stirred for a further 5 h.

The resulting precipitate was then filtered off with suction and washed 3× with 50 ml of methanol each time. 141.8 g of moist doxazosin mesylate (modification D) were obtained. This corresponds to 89.2 g of dry substance and a yield of 93.1%.

Examples of Pharmaceutical Forms 121 g of doxazosin mesylate (form D), 5 g of Aerosil® (highly dispersed silica) and 874 g of spray-dried lactose were mixed together, and the resulting mixture was ground and triturated in a laboratory pinned disk mill. It was important to produce a trituration so that the tablets maintain good content uniformity. The trituration obtained in this way was used as base mix for the following formulations:

A. Tablets Containing 1 mg of Doxazosin Mesylate (Modification D)

10 g of the base mix were mixed with 89 g of Ludipress® (excipient preparation from BASF Aktiengesellschaft) and 1 g of magnesium stearate and compressed in an eccentric press with a tablet punch diameter of 7 mm under a force of 8 kN to tablets weighing 100 mg and having a hardness of 80 N. The active ingredient content per tablet was 1.21 mg of doxazosin mesylate, equivalent to 1 mg of doxazosin base. The resulting tablets disintegrated within 2 min in water at 20° C. The active ingredient release after 20 min was 85%.

B. Tablets Containing 2 mg of Doxazosin Mesylate (Modification D)

Tablets weighing 200 mg were produced as in A. They were compressed using a punch with a diameter of 9 mm under a force of 9 kN and had a hardness of 60 N. The doxazosin mesylate content of the tablet was 2.42 mg, equivalent to 2 mg of doxazosin base. The tablets obtained in this way disintegrated within 3 min in water at 20° C. The active ingredient release after 20 min was 81%.

C. Tablets Containing 4 mg of Doxazosin Mesylate (Modification D)

20 g of the base mix were mixed with 79 g of Ludipress® (excipient preparation from BASF Aktiengesellschaft) and 1 g of magnesium stearate and compressed in an eccentric press with a tablet punch diameter of 9 mm under a force of 8 kN to tablets weighing 200 mg and having a hardness of 50 N. The active ingredient per tablet was 4.84 mg of doxazosin mesylate, equivalent to 4 mg of doxazosin base. The resulting tablets disintegrated within 4 min in water at 20° C. The active ingredient release after 20 min was 80%.

The release in vitro was determined by the following method:

The tablets were tested for their active ingredient release in a paddle apparatus complying with USP XXIII with 6 individual release vessels. The individual vessels contained 900 ml of a 0.08 molar HCl solution. The stirring speed was 50 rpm. The temperature was 37° C. The number of tablets tested was 6 tablets per dose. After 20 min, 100 ml of solution were removed and filtered through a filter (0.5 $\mu$m). This solution was used without further dilution for direct determination of the amount of doxazosin mesylate dissolved out of the tablets. The active ingredient was determined using a UV spectrophotometer at a wavelength of 245 nm.

The extinctions when the active ingredient has dissolved quantitatively should be: 1 mg dose: E 0.116, 2 mg dose: E 0.231 and 4 mg dose: E 0.462.

We claim:

1. A solid pharmaceutical form comprising modification D of doxazosin mesylate, wherein the modification D of doxazosin mesylate is characterized by lines in an X-ray diffractogram at the following values of 2 theta: 5.72±0.2°; 11.10±0.2°; 11.46±0.2°; 14.14±0.2°; 17.01±0.2°; 17.78±0.2°; 18.33±0.2°; 20.73±0.2°; 21.70±0.2°; 23.12±0.2°; 24.28±0.2°; 26.58±0.2°.

2. A method of producing solid pharmaceutical forms for treatment of high blood pressure comprising admixing modification D of doxazosin mesylate as claimed in claim 1 with excipients and compressing the mixture into tablets.

* * * * *